United States Patent [19]

Nelson

[11] Patent Number: 4,683,321

[45] Date of Patent: Jul. 28, 1987

[54] PREPARATION OF DIALKYLDIALKOXYSILANES AND RELATED COMPOUNDS

[75] Inventor: Gunner E. Nelson, Baton Rouge, La.

[73] Assignee: Ethyl Corporation, Richmond, Va.

[21] Appl. No.: 923,184

[22] Filed: Oct. 27, 1986

[51] Int. Cl.$^4$ ............................................. C07F 7/18
[52] U.S. Cl. ................................................. 556/478
[58] Field of Search ..................................... 556/478

[56] References Cited

U.S. PATENT DOCUMENTS

| | | | |
|---|---|---|---|
| 2,762,824 | 9/1956 | Brown | 556/478 |
| 2,857,414 | 10/1958 | Schmidt et al. | 556/478 X |
| 3,004,079 | 10/1961 | Sleddon et al. | 556/478 X |
| 3,398,171 | 8/1968 | Giraitis et al. | 556/478 |
| 4,595,777 | 6/1986 | Bakshi et al. | 556/478 |

*Primary Examiner*—Paul F. Shaver

*Attorney, Agent, or Firm*—Donald L. Johnson; John F. Sieberth; Robert A. Linn

[57] ABSTRACT

Alkali metal aluminum tetraalkyls can alkylate tetraalkyl silicates and alkyltrialkoxysilanes, $Si(OR)_4$ and $RSi(OR)_3$, respectively. The product in each case is predominately the dialkylate. With tetraalkyl silicates, both of the alkyl groups bonded to silicon in the dialkylate product are derived from the metal tetraalkyl. With alkyltrialkoxysilanes, the silicon atom in the dialkylate product is (a) bonded to one alkyl group detained from the metal tetraalkyl, and (b) is also bonded to an alkyl group—that was bonded to silicon—in the silicon-containing starting material. Thus, the alkyl groups in the dialkylate product that are bonded to silicon can be alike or different. The dialkyldialkoxysilane products produced by this invention can be reduced to the corresponding silanes; e.g., $R_2SiH_2$, by using an alkyl aluminum tetrahydride as the reducing agent. The dialkyldialkoxysilanes as well as the dialkylsilanes produced are useful as chemical intermediates.

5 Claims, No Drawings

PREPARATION OF DIALKYLDIALKOXYSILANES AND RELATED COMPOUNDS

BACKGROUND OF THE INVENTION

1. Field of the Invention

This invention pertains to the preparation of organic derivatives of silicon. It also pertains to use of alkali metal aluminum tetraalkyls as alkylating agents.

2. Description of Prior Art

It is known that tetraalkyl silicates are alkylated by trialkylaluminums at high temperature with or without a solvent, and that a mixture of products results. For example, triethyl aluminum etherate heated with tetrabutyl silicate at 190°–200° C. gives $Et_3SiOBu$ (20%), $Et_2Si(OBu)_2$ (45%) and $EtSi(OBu)_3$, along with diethylaluminum butoxide and ether; *Organoaluminum Compounds*, Mole and Jeffrey, Elsevier (1972), page 387.

SUMMARY OF THE INVENTION

Alkali metal aluminum tetraalkyls can alkylate tetraalkyl silicates and alkyltrialkoxysilanes, i.e. $Si(OR)_4$ and $RSi(OR)_3$, respectively. The product in each case is predominately the dialkylate, i.e. a dialkyldialkoxysilane, $RRSi(OR)_2$. With use of tetraalkyl silicates, both of the alkyl groups bonded to silicon in the dialkylate product are derived from the metal tetraalkyl. With alkyltrialkoxysilanes, the silicon atom in the dialkylate product is bonded to (a) one alkyl group obtained from the metal tetraalkyl, and (b) another alkyl group contributed by the silicon-containing starting material. Thus, the alkyl groups in the dialkylate product (that are bonded to silicon) can be alike or different.

The dialkyldialkoxysilane products produced by this invention are useful as chemical intermediates. For example, they can be reduced to the corresponding dialkylsilanes by using an alkali metal aluminum tetrahydride as the reducing agent. The dialkylsilanes ($R_2SiH_2$) so produced are also useful as chemical intermediates.

DESCRIPTION OF PREFERRED EMBODIMENT

A highly preferred embodiment of this invention is a process for preparing a dialkyldialkoxysilane, $R^1R^2Si(OR^3)_2$, said process comprising reacting an alkali metal aluminum tetraalkyl, $MAlR^1_4$, with a silicon-containing reactant selected from the class consisting of:

(i) tetraalkyl silicates, $Si(OR^3)_4$, and
(ii) alkyltrialkoxysilanes, $R^2Si(OR^3)_3$, wherein $R^1$ is an alkyl radical of 2–18 carbons, $R^2$ is an alkyl radical of 1–18 carbons, $R^3$ is an alkyl radical of one to four carbon atoms, and M is an alkali metal selected from lithium, sodium, and potassium.

The alkali metal aluminum tetraalkyl, $MAlR^1_4$, used as a reactant can be $LiAlR_4$, $NaAlR_4$ or $KAlR_4$. Mixtures of these materials can also be used. The sodium compounds are preferred because of their ready availability. Preferably, each group represented by $R^1$ in these compounds is the same. The sodium aluminum complex can be used in a dissolved state; this is preferred since it facilitates contact with the other reactant. In a preferred embodiment, the complex is dissolved in the olefin from which it is derived.

As indicated above, preferred reactants have the molecular formula $NaAlR^1_4$. The radical $R^1$ can have one or more carbons. Since the $MAlR^1_4$ complexes are readily prepared from olefins, $R^1$ usually has at least two carbon atoms. Preferably, the alkyl radicals have 4 to 18 carbon atoms, and most preferably 6–12 carbons. The number of carbon atoms in each alkyl group can be odd or even.

As with the alkyl groups in the alkali metal aluminum tetraalkyl reactants, the nature and size of the alkyl groups in the tetraalkyl silicate, and in the alkyltrialkoxysilane reactants are not critical. Preferably these groups are readily formed at an acceptable cost, and of a size, nature, and configuration such that they do not hinder the desired reaction by steric hindrance, or by causing an unacceptable amount of extraneous side reactions. Thus, it is preferred that the groups be hydrocarbyl radicals, i.e. solely composed of carbon and hydrogen, that they be acyclic, and that they be straight chain, or have relatively little branching. They may have up to 18 or more carbon atoms.

In many instances, the product of this process is used as an intermediate. Frequently, the alkoxy groups in the product are removed, and other group(s) substituted therefor. For economical reasons in these instances, it is preferred that the alkoxy radicals within the $Si(OR)_4$ and $RSi(OR)_3$ reactants be derived from small alkyl groups; say those containing from one to four carbon atoms.

The $RSi(OR)_3$ reactants are especially useful reactants in the process of this invention when an object is to prepare a dialkyldialkoxysilane having dissimilar R groups bonded to silicon. In these instances, a practitioner will select a reactant, $MAlR^1_4$, wherein the radical $R^1$ is different from $R^2$ in the reactant depicted by $R^2Si(OR^3)_3$. Also, reactants having the formula $CH_3Si(OR^3)^3$ are especially useful when the product of this invention is to have a methyl group bonded to silicon.

In light of such considerations as given above, it is highly preferred that in the materials utilized as reactants in this invention and depicted by the formulas: $MAlR^1_4$, $R^2Si(OR^3)_3$, and $Si(OR^3)_4$, that any group depicted by:

--$R^1$, be an alkyl radical of 2–18 carbon atoms,
--$R^2$, be an alkyl radical of 1–18 carbon atoms, and
--$R^3$, be an alkyl radical of 1–4 carbon atoms.

However, a skilled practitioner will recognize that there is no real upper limit on the size of the alkyl groups, and radicals having a greater number of carbon atoms are to be considered equivalents to those mentioned above. A skilled practitioner will also note that while the above description focuses on reactants with alkyl groups, reactants having other organic radicals, such as aryl, alkaryl and aralkyl, can also be used in the invented process. For this invention, these other organic radicals should be groups that are: (a) stable under the reaction conditions employed, (b) not so bulky as to unduly retard the reaction by steric hindrance, and (c) not possessed of chemical structures or properties that cause an unacceptable amount of extraneous side reactions when utilized in the process of this invention.

The process of this invention is carried out by contacting the reactants under reaction conditions. The reactants need not be contacted neat, they may be used in the presence of other substances, such as an inert liquid reaction medium. For example, the $MAlR_4$ reactant can be utilized in the presence of olefin from which it is derived. For example, it may be used as a 30% or more concentrated solution in the olefin; typically, the concentration is 30-50%. Therefore, depending on the metal complex used, the process may be conducted in the presence of olefin(s) having up to 18 carbon atoms. In many instances the olefin will be an alpha olefin such as:
hexene-1
octene-1
decene-1
dodecene-1

It is not necessary that the olefin have an even number of carbons; however, these materials are commercially available by chain growth of ethylene, and also by isolation from natural products. Because of their availability, even numbered olefins are preferred materials for making the MAlR$_4$ reactants used in this invention. However, olefins with an odd number of carbons can also be used. Mixtures of olefins, as well as pure, or substantially pure olefins can be used to prepare the MAlR$_4$ reactant, and also serve as reaction media in this invention.

The process of this invention can be conducted in the presence of other inert ingredient(s) that do not materially interfere with the course of the reaction. Thus for example, the process may also be conducted in the presence of an inert liquid paraffinic hydrocarbon such as hexane, heptane, octane, decane, or similar substance. Such substances may be used to increase the volume of the liquid phase and thereby facilitate contacting the reactants.

As stated above, the materials in the reaction mixture are contacted under reaction conditions; i.e., under conditions that cause the desired reaction to take place. Somewhat elevated temperatures are used, generally these are in the range of from about 150° to about 250° C. In many instances, a temperature range of about 160° to about 200° C. is preferred. The process is facilitated by conducting it under pressure. Endogenous pressures are usually satisfactory; the materials are added to a pressure vessel, the vessel sealed, and the vessel then brought to desired reaction temperature. Pressures can be increased if desired by pressuring the vessel with nitrogen, argon or other inert gas. Although pressures in the range of from about 50 psig to about 300 psig are satisfactory; preferably, pressures from about 75 psig to about 150 psig are used. Higher or lower pressures can be employed if desired. Stirring, rocking or other means of agitating material in the reaction vessel, facilitates contacting the reactants and is a preferred, but not critical, process expedient.

The time of reaction is not a truly independent variable, but is dependent at least to some extent on the other reaction conditions employed. In general, higher pressures and temperatures give shorter reaction times. Usually the reaction is complete in less than two days (48 hours). It is convenient in many instances to run the reaction overnight. When using preferred reaction conditions, the reaction is usually complete in 2-20 hours.

The reactants can be combined in any relative quantity; i.e., molar ratio that will permit the reaction to proceed. By simple experiment a skilled practitioner can determine if a particular molar ratio to be employed will allow the reaction to take place as desired, and in accordance with one of the embodiments set forth herein. For example, when reacting a MAlR$_4$/Si(OR)$_4$ reaction mixture, it is usually desirable to use the reactants in about equimolar quantities. When reacting a MAlH$_4$/RSi(OR)$_3$ reaction mixture, about one-half mole of MAlR$_4$ is employed per each mole portion of RSi(OR)$_3$.

For either reaction, an excess of either reactant can be used to assist the reaction; therefore, an excess of up to 5, 10 or more mole portions of either reactant can be used, if desired. In many instances however, use of large quantities of excess reactant serves no useful purpose, and makes the process unnecessarily expensive.

EXAMPLE I

To a suitable reaction vessel was added 28.2 millimoles of NaAl(C$_8$H$_{17}$)$_4$ as a 40% solution in octene-1. To this was added 5.26 grams (25.3 millimoles) of ethyl orthosilicate, Si(OC$_2$H$_5$)$_3$. The vessel was closed, the stirrer activated, and the mixture heated overnight (20 hours) using an oil bath at 170° C.

The mixture was cooled and poured onto about 200 grams of ice. Fifty milliliters of hexane was added to increase the volume of the organic phase. The organic phase was separated, washed with water and dried over Na$_2$SO$_4$. Two products were evidenced by gas liquid chromatography.

Using gas chromatography/mass spectrographic analysis, the two products were shown to be C$_8$H$_{17}$Si(OC$_2$H$_5$)$_3$ and (C$_8$H$_{17}$)$_2$Si(OC$_2$H$_5$)$_2$; a trace of (C$_8$H$_{17}$)$_3$SiH was also identified. After stripping the solvent, a sample was mixed with naphthalene as an internal standard. Gas phase chromatography showed the yields to be (C$_8$H$_{17}$)Si(OC$_2$H$_5$)$_3$, 25.9%, and (C$_8$H$_{17}$)$_2$Si(OC$_2$H$_5$)$_2$, 33.8%. No correction was made for material within the gas phase/mass spectrographic analysis sample.

As demonstrated by this example, the process of this invention can be conducted to prepare an appreciable yield of monoalkyltrialkoxysilane, such as C$_8$H$_{17}$Si(OC$_2$H$_5$)$_3$. It is believed that in the formation of dialkyldialkoxysilanes such as (C$_8$H$_{17}$)$_2$Si(OC$_2$H$_5$)$_2$, the monoalkyltrialkoxysilane is made first, and then further alkylated to form the dialkyldialkoxysilane product.

It is believed that generally, the dialkyldialkoxysilanes R$^1$$_2$Si(OR$^3$)$_2$ produced as exemplified above, are more valuable intermediates than the monoalkyltrialkoxysilanes, R$^1$Si(OR$^3$)$_3$. Accordingly, it is preferred to conduct the process to favor preparation of the dialkylated product. However it is to be understood that the invention encompasses a process for: (a) formation of RSi(OR)$_3$ products, (b) products that comprise mixtures of RSi(OR)$_3$ and R$_2$Si(OR)$_2$, and (c) R$_2$Si(OR)$_2$ products, said process comprising the reaction of orthosilicates Si(OR)$_4$ and alkali metal aluminum tetralkyls MAlR$_4$, wherein M is Li, Na, or K, and each R can be alike or different.

In light of the above, a skilled practitioner can appreciate that this invention also comprises a two-step procedure:
(a) Reaction of an orthosilicate Si(OR)$_4$ with an alkali metal aluminum alkyl, MAlR$_4$, to form a monoalkyltrialkoxysilane, RSi(OR)$_3$; and
(b) Reaction of the RSi(OR)$_3$ product of the first step with another MAlR$_4$ reactant to form a dialkyldialkoxysilane with two different alkyl groups directly bonded to silicon, R$^1$R$^1$Si(OR)$_2$.

EXAMPLE II

Following the procedure of Example I, 37.7 grams of "crude" NaAl(C$_8$H$_{17}$)$_4$, used as prepared, unfiltered, (40% by weight solution in octene-1) and 8.75 grams of ethyl orthosilicate were reacted overnight at 190° C. The products produced were (C$_8$H$_{17}$)$_2$Si(OC$_2$H$_5$)$_2$, 53.8%; (C$_8$H$_{17}$)$_3$Si(OC$_2$H$_5$), 16.4%; and (C$_8$H$_{17}$)$_3$SiH, 4.5%. These analytical results were obtained using gas phase chromatography with naphthalene as an internal standard.

The procedure of the above example can be repeated using the potassium or lithium complex corresponding to the sodium aluminum tetraalkyl that was employed. The procedure of the example can be modified by conducting the process at 160° for twenty hours or 200° C. for 5 hours; similar results are obtained. The process can also be extended to use of metal aluminum tetraalkyls such as the lithium, sodium and potassium compounds having the formula $MAlR^1_4$ wherein $R^1$ is, ethyl, n-butyl, n-hexyl, n-octyl, n-decyl, n-dodecyl, D-tetradecyl, n-hexadecyl or D-octadecyl. The corresponding dialkyldialkoxysilane products, viz $R^1{}_2Si(OR^3)_2$ are obtained. Likewise, the process can be extended to use of other orthosilicates $Si(OR^3)_4$ wherein $R^3$ is methyl, n-propyl, n-butyl, and the like. The corresponding dialkyldialkoxysilanes are formed.

EXAMPLE III

Following the procedure of the Examples above, 44.7 millimoles of $NaAl(OC_8H_{17})_4$ and 37.0 millimoles of $Si(OC_2H_5)_4$ were reacted at 150° C. The products and yields were as follows:

| | |
|---|---|
| $C_8H_{17}Si(OC_2H_5)_3$ | 39.3% |
| $(C_8H_{17})_2Si(OC_2H_5)_2$ | 22.6% |

EXAMPLE IV

Following the procedures of the above examples, 46.7 millimoles of $NaAl(C_8H_{17})_4$ in octene-1 solution were reacted with 38.9 millimoles of $Si(OC_2H_5)_4$, by stirring overnight at 190° C. The products and yields were as follows:

| | |
|---|---|
| $(C_8H_{17})_2Si(OC_2H_5)_2$ | 53.4% |
| $(C_8H_{17})_3Si(OC_2H_5)$ | 2.5% |
| $(C_8H_{17})_3SiH$ | 6.1% |

Compared to the preceding example, it can be seen that the increased temperature markedly increased the yield of the dialkyldialkoxysilane $(C_8H_{17})_2Si(OC_2H_5)_2$ from 39.3% to 53.4%, at the expense of monoalkyl product. Thus, the higher temperature increased the ability to form disubstituted product to such an extent, that no monosubstituted product was isolated. In contrast, the reaction at 150° C. resulted in a 39.3% yield of the monosubstituted product, $C_8H_{17}Si(OC_2H_5)_3$.

Furthermore, when the results of this example are compared with Example II, it can be seen that much more trialkylalkoxysilane was formed in that example. Thus it appears the formation of the trialkyl product may be promoted by some species in the impure $NaAl(OC_8H_{17})_4$, perhaps titanium.

EXAMPLE V

Sodium aluminum tetraoctyl, $NaAl(OC_8H_{17})_4$, 46.0 millimoles (40% solution in octene-1) and 38.3 millimoles of tetraethyl orthosilicate were reacted with stirring for:

7 hours at 150° C.,
4 hours at 170° C.,
2 hours at 180° C., and
5 hours at 190° C.

The resultant mixture was then cooled. An 8 ml portion of a dimethoxyethane solution of $NaAlH_4$ containing 2.5 millimoles of hydride per ml was added. The reaction mass was heated for an hour at 110° C., and then hydrolyzed and worked up as described previously. Using naphthalene as an internal standard (as in Examples I-IV) it was demonstrated that the product contained 7.7 grams of dioctylsilane, $(C_8H_{17})_2SiH_2$ and 1.0 grams of trioctylsilane, $(C_8H_{17})_3SiH$.

The product solution was distilled under vacuum and a heart cut was distilled at 105° C./0.5 mm Hg. It was shown by gas phase chromatography to be 98.4% dioctyl silane, $(C_8H_{17})_2SiH_2$. The yields were:

| | |
|---|---|
| $(C_8H_{17})_2SiH_2$ | 64.1% |
| $(C_8H_{17})_3SiH$ | 6.6% |

The process of this example demonstrates that the alkoxysilane product fraction produced by this invention need not be isolated, and that it can be used for further reaction in the reaction mixture in which it is produced. Furthermore, the dialkyl and trialkylsilanes are much easier to isolate than the alkoxysilanes from which they are made. Since the reduction is also essentially quantitative in many instances, analysis of the reduced product usually gives a better indication of the extent of reaction than work-up of the alkoxysilane products.

EXAMPLE VI

A mixture of 69.1 mmoles of $NaAl(C_8H_{17})_4$ as a 35% solution in octene-1 and 8.6 grams (41.2 mmoles) of tetraethyl orthosilicate was heated at 185°–190° C. for 5 hours. After cooling to room temperature, 9 ml of $NaAlH_4$ in dimethoxymethane (2.5 mmoles per ml) was added, and the resultant mass was heated to 120° C. for one hour.

The mixture was cooled to room temperature, and hydrolyzed with 50 ml of 3N NCl. The separated organic phase was washed with 50 ml of 3N NCl and 50 ml of $H_2O$ and dried over $MgSO_4$. The organic fraction, 74.3 grams, analyzed by gas phase chromatography (GC) contained:

| Product | Amount | | Yield |
|---|---|---|---|
| $(C_8H_{17})SiH_2$ | 8.83 g | 34.49 mmoles | 83.7% yield |
| $(C_8H_{17})SiH$ | 1.92 g | 5.23 mmoles | 12.7% yield |

The reduction step employed in the above example can be modified by using—instead of $NaAlH_4$—one or more of the following reducing agents, $LiAlH_4$, $KAlH_4$, $LiH$, $NaH$ or $KH$. The reduction can be conducted between 90° and 120° C., using a reaction time of 0.5–2.0 hours.

EXAMPLE VII

The following mixture was added to a pressure vessel:

| | | |
|---|---|---|
| $NaAl(C_{10}H_{21})_4$ | 43.1 g | 31.13 mmoles |
| $CH_3Si(OCH_3)_3$ | 8.4 g | 61.67 mmoles |
| nonane | ~10 ml | | and reacted at 190° C. for 5 hours. After cooling, there was added 15 ml of $NaAlH_4$ in dimethoxyethane (DME); i.e., ~33 meq of the hydride. The reaction mass was heated in the closed vessel for one hour at 115°–120° C.

The resultant mixture was cooled, hydrolyzed with 3N HCl, and then washed with 50 ml of 3N HCl. The organic phase was separated and dried over MgS$_4$. The MgSO$_4$ was removed by filtration and washed with heptane to facilitate transfer. The organic phase plus heptane washings totaled 114 grams.

Using naphthalene as an internal standard, GC analysis showed the product contained 10.58 grams of methyl(decyl)silane, $CH_3Si(C_{10}H_{21})H_2$, 92.3% yield. This demonstrated that the initial conversion (before reduction) to methyl(decyl)dimethoxysilane, $CH_3Si(C_{10}H_{21})(OCH_3)_2$, was high—92.3%, if the reduction was quantitative.

EXAMPLE VIII

Following the procedure of the previous example, 45.7 grams, of a solution of $NaAl(C_{10}H_{21})_4$ in decene-1 containing 1.91% Al, i.e. 32 mmoles of the aluminum compound, was charged to a pressure vessel with 11.98 g, 88 mmoles of $CH_3Si(OCH_3)_3$. The mixture was reacted with stirring at 190% for five hours. The mixture was cooled, transferred to a 500 ml round bottom flask and 20 ml of NaAlH$_4$ in DME (~44 mmoles) was added.

The reaction mixture was cooled in ice water, hydrolyzed with 3N HCl, and the organic phase washed with 100 ml of 3N HCl and dried over MgSO$_4$. The yield of $CH_3Si(C_{10}H_{21})H_2$ was 71.6 mmoles, 81.4% of theory.

EXAMPLE IX

The following charge was added to a suitable pressure vessel:
- 70.9 g of $NaAl(C_{10}H_{21})_4$ as a decane solution with an Al concentration of 1.93%, 50.68 mmoles,
- 18.4 g of $CH_3Si(OCH_3)_2$, 135 mmoles, and
- 20 ml of nonane, and then reacted with stirring for 5 hours at 190° C. The mixture was discharged to a 500 ml round bottom flask using 100 ml of heptane as a wash.

The mixture was treated with 40 ml of CH$_3$OH and stirred for two hours at room temperature. Samples of the hydrocarbon and methanol layers were analyzed by gas chromatography/mass spectrophotographic analysis and the results were as follows:

|  | Hydrocarbon Layer | Methanol Layer | Total Yield |
|---|---|---|---|
| $CH_3Si(C_{10}H_{21})(OCH_3)_2$ | 68.0% | 10.6% | 78.6% |
| $CH_3Si(C_{10}H_{21})_2(OCH_3)$ | 5.6% | | |

The methyl(decyl)dimethoxysilane was distilled at 128.3 at 5 mm Hg and yielded 21.8 grams of product distillate.

The procedure of the above example, before the reduction step using NaAlH$_4$, can be repeated using the potassium or lithium complex corresponding to the sodium aluminum tetraalkyl that was employed. The procedure of the example can be modified by conducting the process at 160° for twenty hours or 200° C. for 5 hours; similar results are obtained. The process before the reduction step can also be extended to use of metal aluminum tetraalkyls such as the lithium, sodium and potassium compounds having the formula MAlR$^1_4$ wherein $R^1$ is, ethyl, n-butyl, n-hexyl, n-octyl, n-dodecyl, n-tetradecyl, n-hexadecyl or n-octadecyl. The corresponding product dialkyldialkoxysilane $(CH_3)R^2Si(OR)_2$, is obtained.

The process of the above example before the reduction step can be repeated using as a reactant a compound having the formula $CH_3Si(OR^3)_3$ wherein $R^3$ is methyl, propyl, n-butyl, and the like. The corresponding dialkyldialkoxysilane is formed wherein the radicals (OR$^3$) have the alkyl group, R$^3$, within the starting methyltrialkoxysilane.

Likewise, the process of the above example before the reduction step can be extended to use, as a reactant, a compound having the formula $R^2Si(OCH_3)_3$ wherein R$_2$ is ethyl, n-butyl, D-hexyl, n-octyl, D-decyl, n-dodecyl, n-tetradecyl, n-hexadecyl, and n-octadecyl. The corresponding dialkyldialkoxysilane is obtained wherein one of the radicals depicted by R$^2$ in the formula $R^2R^2Si(OR^3)_2$ is an alkyl group derived from the alkali metal aluminum alkyl MAlR$_4$, and the other is the alkyl group bonded directly to silicon in the alkyltrialkoxysilane starting material, $R^2Si(OR^3)_3$.

If desired, the reduction step of the previous example can be modified by using instead of NaAlH$_4$, a reductant selected from LiAlH$_4$, KAlH$_4$, LiH NaH, and KH. The reduction can be conducted at a temperature of 90°–120° C. for one-half to about two hours.

It is to be understood that a skilled practitioner can modify the reactant conditions or the reactants described above and still be within the metes and bounds of this invention. For example, one may wish to use a low reaction temperature and/or short reaction time to favor the formation of an $R^1Si(OR^3)_3$ product, rather than the corresponding dialkylalkoxysilane, $R_2Si(OR^3)_2$ when reacting an alkali metal aluminum tetraalkyl with an orthosilicate. Likewise, one may wish to use an alkali metal aluminum alkyl where the four alkyl groups are not all the same, or use an orthosilicate or an alkyltrialkoxysilane starting material in which the alkoxy groups are not all identical. Such changes, and the products produced thereby, are modifications, considered to be equivalents of the embodiments described above, and therefore wholly within the intended scope and spirit of the following claims.

I claim:
1. A process for preparing a dialkyldialkoxysilane, $R^1R^2Si(OR^3)_2$, said process comprising reacting an alkali metal aluminum tetraalkyl, MAlR$^1_4$, with a silicon-containing reactant selected from the class consisting of:
   (i) tetraalkyl silicates, Si(OR$^3$)$_3$, and
   (ii) alkyltrialkoxysilanes, $R^2Si(OR^3)_3$,
   wherein R$^1$ is an alkyl radical of 2–18 carbons, R$^2$ is an alkyl radical of 1–18 carbons, R$^3$ is an alkyl radical of 1–4 carbon atoms, and M is an alkali metal selected from lithium, sodium, and potassium.
2. The process of claim 1 wherein said silicon-containing reactant is a tetraalkyl silicate, Si(OR$^3$)$_4$.
3. The process of claim 1 wherein said silicon containing reactant is an alkyltrialkoxysilane, $R_2Si(OR^3)_3$.
4. The process of claim 1 wherein said alkali metal tetraalkyl is a sodium compound, NaAlR$^1_4$.
5. The process of claim 1 being conducted at from about 160° to about 200° C.

* * * * *

UNITED STATES PATENT AND TRADEMARK OFFICE
CERTIFICATE OF CORRECTION

PATENT NO.   : 4,683,321
DATED        : July 28, 1987
INVENTOR(S)  : Gunner E. Nelson It is certified that error appears in the above-identified patent and that said Letters Patent is hereby corrected as shown below:

Column 2, line 35, "$CH_3Si(OR^3)^3$" should read -- $CH_3Si(OR^3)_3$ --.

Column 5, line 14, "D-octadecyl" should read -- n-octadecyl --.

Column 7, line 6, "$MgS_4$" should read -- $MgSO_4$ --.

Column 8, line 15, "D-hexyl" should read -- n-hexyl --.

Column 8, line 15, "D-decyl" should read -- n-decyl --.

Signed and Sealed this

Twenty-fourth Day of November, 1987

Attest:

DONALD J. QUIGG

*Attesting Officer*

*Commissioner of Patents and Trademarks*